United States Patent [19]

Edeland et al.

[11] 4,150,296
[45] Apr. 17, 1979

[54] DEVICE IN CONNECTION WITH X-RAY APPARATUS FOR DENTAL USE

[75] Inventors: Nils G. Edeland, Tvargatan 5, 691 00, Karlskoga; Lars H. R. Högstedt, Örebro, both of Sweden

[73] Assignee: Gunnar Edeland, Karlskoga, Sweden

[21] Appl. No.: 829,523

[22] Filed: Aug. 31, 1977

[30] Foreign Application Priority Data

Sep. 7, 1976 [SE] Sweden ............................ 7609857-3

[51] Int. Cl.$^2$ .............................................. G03C 5/16
[52] U.S. Cl. ................................................... 250/479
[58] Field of Search ................................ 250/479, 478

[56] References Cited

U.S. PATENT DOCUMENTS 1,657,230  1/1928  Semonton ............................ 250/479
1,667,442  4/1928  Sikes ................................... 250/479

Primary Examiner—Craig E. Church

Attorney, Agent, or Firm—Hane, Roberts, Spiecens & Cohen

[57] ABSTRACT

A holding device for an X-ray plate adapted for mounting on an X-ray tube comprising a ring mountable on the X-ray tube for turning movement thereon. The ring is supported in a groove formed by two auxiliary rings which can lock the ring in a fixed angular position on the tube. A bar is attached by a detachable fastener assembly attached to the ring in a position in which the bar extends parallel to the axis of the tube. The bar is rotatable around its own axis and is longitudinally displaceable in the fastener assembly. The bar extends forwardly from the fastener assembly and has a front end at which there is detachably supported a throwaway X-ray plate-holder extending at right angles to the bar. An X-ray plate is mounted in a slit in the plate-holder and assumes a position at right angles to the axis of the tube.

10 Claims, 6 Drawing Figures

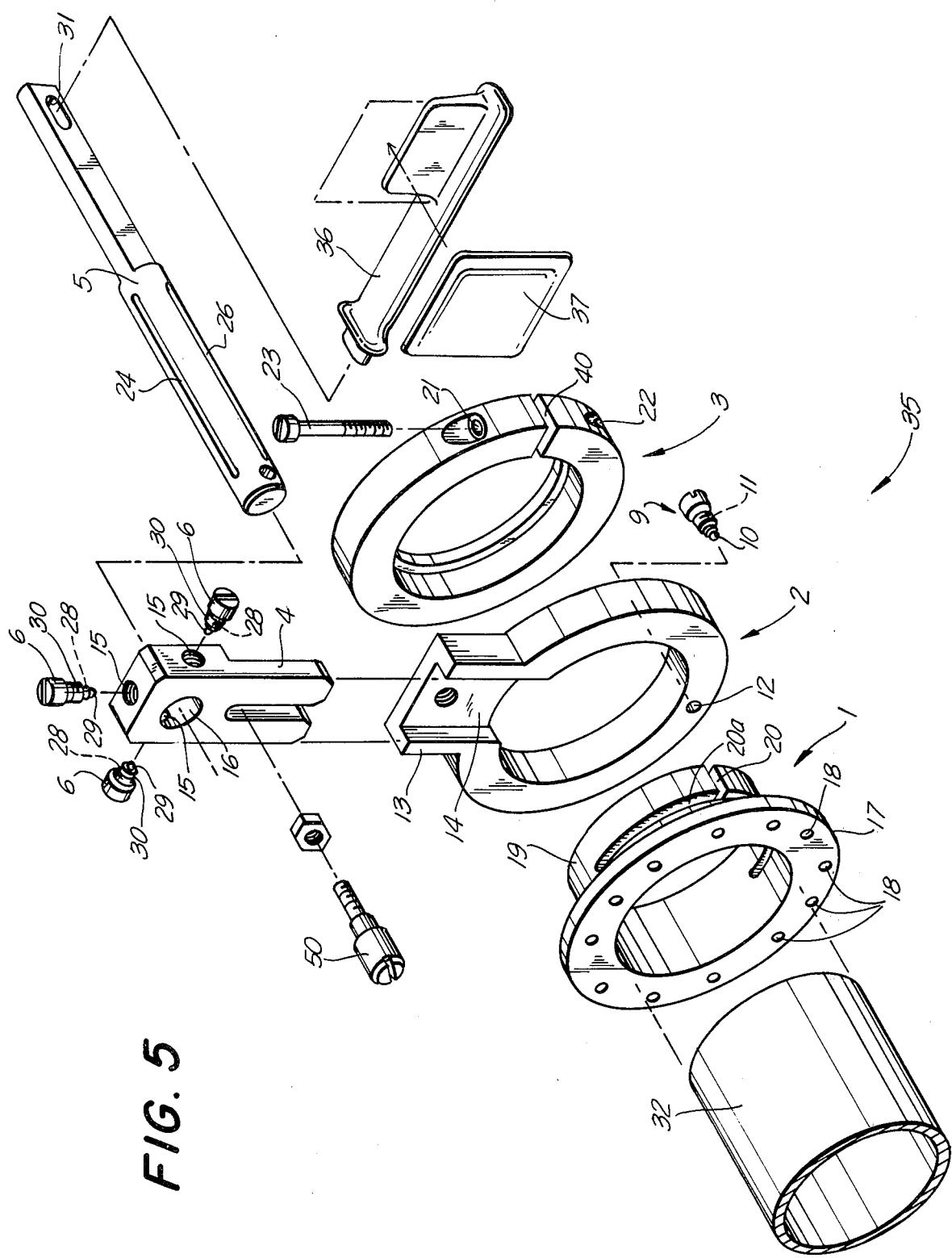

DEVICE IN CONNECTION WITH X-RAY APPARATUS FOR DENTAL USE

FIELD OF THE INVENTION

The present invention relates to a device in connection with X-ray apparatus for dental use.

BACKGROUND OF THE INVENTION

Such pieces of X-ray apparatus are used for intraoral photographing of teeth and oral tissues. In such apparatus, the X-ray apparatus itself is enclosed in a housing which is mounted on gimbals, and the housing has a protruding cone, which will lead the bundle of rays from the X-ray tube against the object which is to be photographed. A plate is placed in the mouth of a patient and the housing is directed in such a way that the rays will hit the plate. In the majority of cases, the patient will hold the plate. This is a drawback, partly because a picture of the patient's finger may disturb the taking, and partly because the plate has a random orientation in relation to the rays. These conditions entail that several photographs may have to be taken before a desired picture is acquired, which results in the drawback that the patient may be exposed to too large doses of X-rays. It is desirable to obtain the desired picture through only one operation, and furthermore, it is desirable for the picture taken to have a certain and standardized orientation in relation to the mentioned protruding cone. If this is the case, and the picture is sent for examination, each dentist who is to interpret the picture will know how the plate was placed in proportion to the X-ray tube when the picture was taken.

In U.S. Pat. No. 3,473,026 it has been proposed to place a ring loosely round the protruding cone, which can hold a bar, which has an axis that substantially coincides with the axis of the cone. The bar has a part which forms an angle with the longitudinal direction of the bar and whereat an X-ray plate has been fastened. This well-known device is difficult to orientate, and in connection with each picture-taking operation it must be placed upon the X-ray cone. Furthermore, the apparatus has the drawback that the bar complete with holder, after taking of pictures of different patients, must be completely replaced by another bar complete with holder. Furthermore, the desired standardized orientation of the plate in relation to the X-ray cone is not acquired.

SUMMARY OF THE INVENTION

An object of the present invention is to provide a device for the X-ray plate, which will eliminate the above-mentioned drawbacks.

According to the invention, a pipe of any cross section is used, for instance rectangular or cylindrical. A circumferential groove is arranged on the outer surface of the pipe. In the circumferential groove is a ring which can be turned and fixed in various positions. The ring is provided with a fastening unit for a bar. The fastening unit is made in such a way that the bar is always parallel with the axis of the pipe. Furthermore, the fastening device is made in such a way that the bar can be turned round its own longitudinal axis and fixed. It is a feature of the fastening unit that the bar can be shifted in its longitudinal direction and fixed in position in the direction of shift. The end of the bar which is situated in front of the free end of the pipe is shaped in such a way that it can detachably receive an X-ray plate holder, which holder is substantially of a disposable character and oriented in such a way that the X-ray plate mainly remains at right angles to the axis of the pipe.

According to the invention, the X-ray plate can thus, in a plane at right angles to the axis of the pipe, move in this plane round the axis of the bar and round the axis of the pipe, and it can also be shifted with respect to the mouth of the pipe to and from the same.

An advantage of the construction according to this invention is that the plate can, in advance, be given a certain position in relation to the front ends of the pipe or the long cone and then be inserted orally into the mouth of a patient, whereby the dentist immediately knows that the plate has the correct position in relation to the X-ray cone.

The X-ray plate holder according to the present invention is suitably made of plastics material and thus it is a disposable article, and therefore it is the only part which it is necessary to replace when pictures are taken of different patients. The result of this is that it will not be necessary to sterilize any part of the X-ray apparatus.

According to the invention, the X-ray plate holder is suitably provided with a slit into which the X-ray plate is inserted. The X-ray plate holder and the axis are preferably designed with female and male parts in order to facilitate the fastening and the removal, respectively, of the X-ray plate holder.

The turning of the ring with fastening unit for the bar, and the turning and shifting of the bar can take place by means of known mechanical elements. The same applies for the fixing of the ring and the bar in the desired position. Therefore, various combinations of structural elements can be used such as a yielding ball in a hole, frictional force between movable elements, toothed and co-operating pawl and toothed segment and toothed wheels.

The above-mentioned groove serves as a holding device for the turnable ring and the holding device can be fastened on the long cone or it can be part of the long cone.

The fact that the holding device for the movable ring is firmly united with the long cone will have the advantage that the distance between the aperture of the diaphragm and the object which is to be photographed can be reduced to less than 30 cm.

According to the invention, it is possible to turn the ring so that it takes up a certain angular position with respect to a predetermined position of reference. The same applies to the turning of the bar, i.e. this also takes up a predetermined angular position when it is twisted into a fixating position.

BRIEF DESCRIPTION OF THE DRAWINGS

FIG. 5 is an exploded perspective view of the holding device;

DETAILED DESCRIPTION

Figure 1:
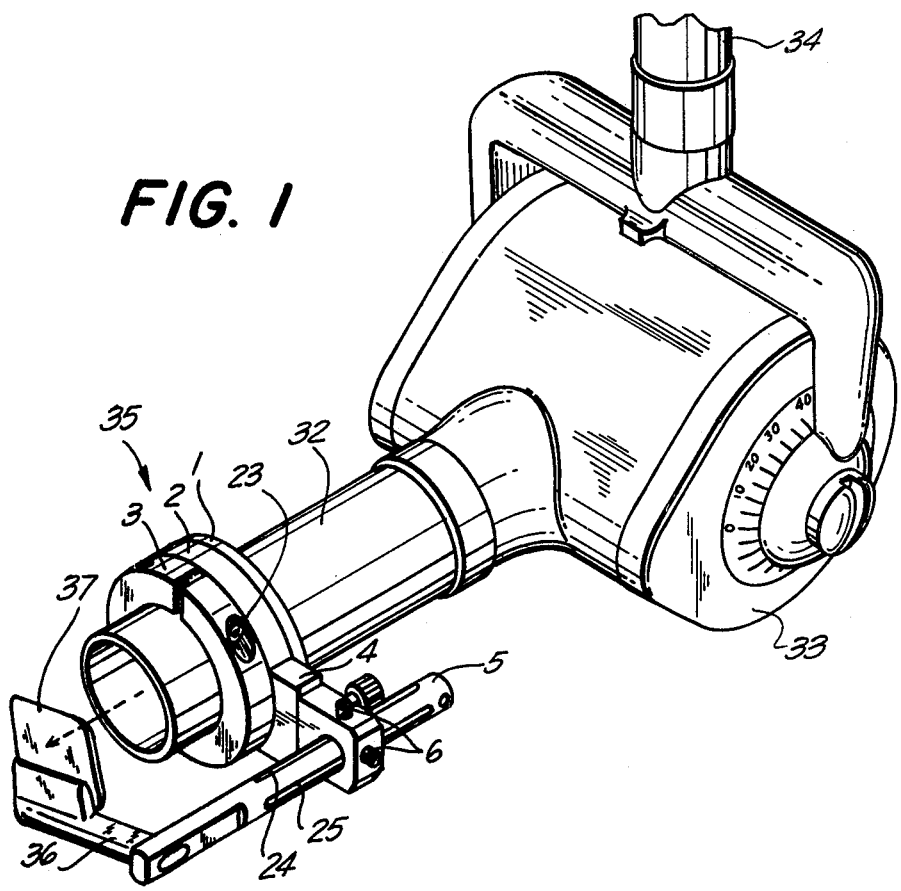
FIG. 1 is a perspective view from above of a portion of dental X-ray equipment showing the holding device of the invention attached to the long cone.
Figure 6:
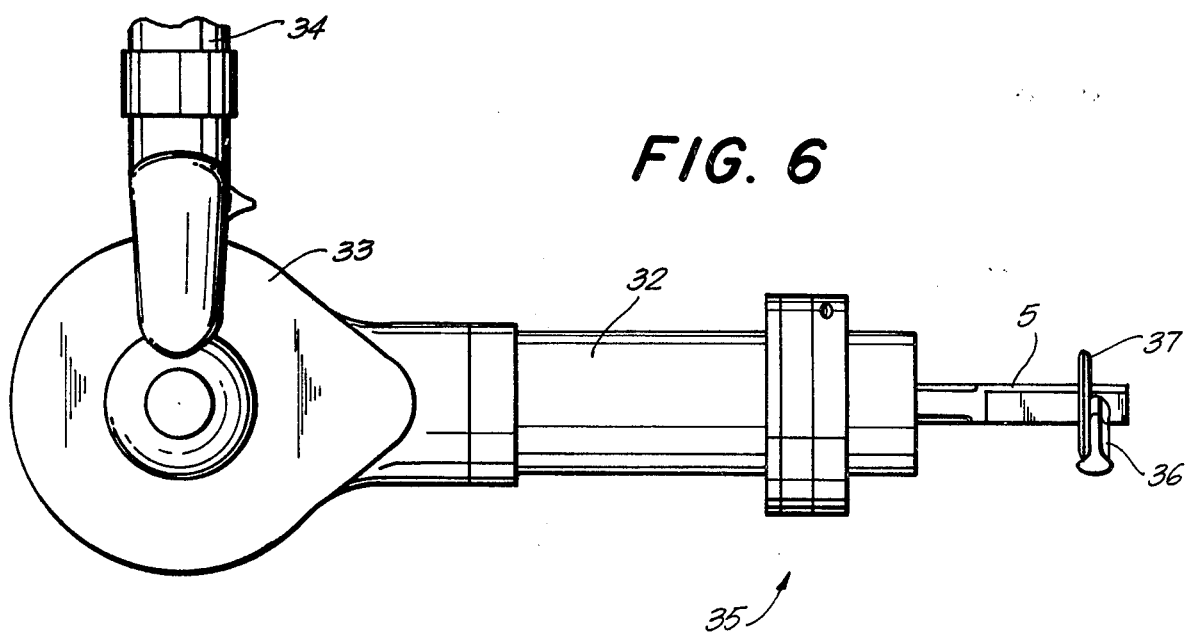
FIG. 6 is an elevational view of the holding device.

Referring to FIG. 1 of the drawing, therein is seen a holding arm 34 on which a housing 33 is mounted on gimbals, which contains an X-ray tube. Firmly united with the housing, for instance, by means of screwing, is one end of a long cone 32, which in the present case is of circular cross section. The long cone can also be of rectangular cross section. Firmly fastened to the outer surface of the long cone is a holding device 35, which consists of two rings 1 and 3. The two rings form a groove. A ring 2 is turnably arranged in the groove, so that the ring 2 can be turned round its axis and round the axis of the long cone. The ring 2 is provided with a fastening unit 4 for a bar 5. The bar 5 can be turned round its axis and be shifted in its longitudinal direction.

At its end in front of the free end of the long cone 32, the bar 5 is provided with a female part, which can receive the male part of an X-ray plate holder 36, which has a slit, into which an X-ray plate 37 of rectangular shape can be fastened. By means of the ring 2 the bar 5 can move like a generatrix round the long cone 32. Furthermore, the bar 5 can be turned round its axis and it can be shifted longitudinally. The X-ray plate holder is made in such a way that the placed X-ray plate 37 is always at a right angle to the axis of the long cone and to the axis of the bar, which is always parallel with the axis of the long cone. By means of the two possibilities of turning the X-ray plate can always be set into a suitable position in relation to the patient, so that the X-ray plate will always be placed in front of the opening of the long cone and substantially within the circumference thereof.

When the picture is taken, only the X-ray plate holder 36 is inserted orally into the patient. Therefore, only the X-ray plate holder will have to be sterilized, and only if this is not a disposable article. The other parts of the device according to the present invention need not be sterilized, and the device according to the present invention is always ready for the taking of pictures. It will only be necessary to place an X-ray plate holder with X-ray plate on the bar 5.

The operation of the holding device 35, the construction of the holding unit, and the special properties of the bar will be described in further detail in the following.

Figure 2:
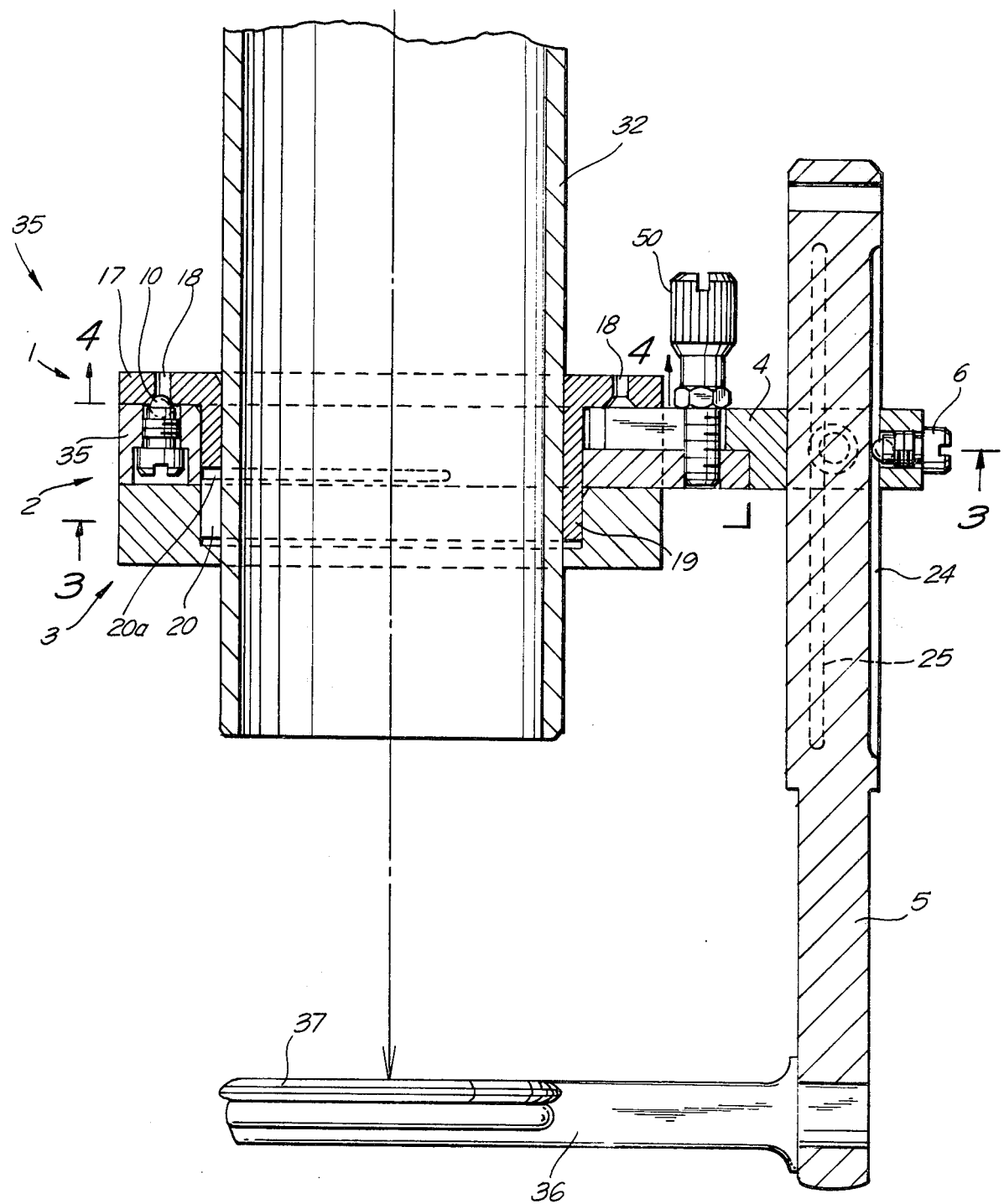
FIG. 2 is a sectional view on enlarged scale of the holding device and a portion of the long cone.
Figure 3:
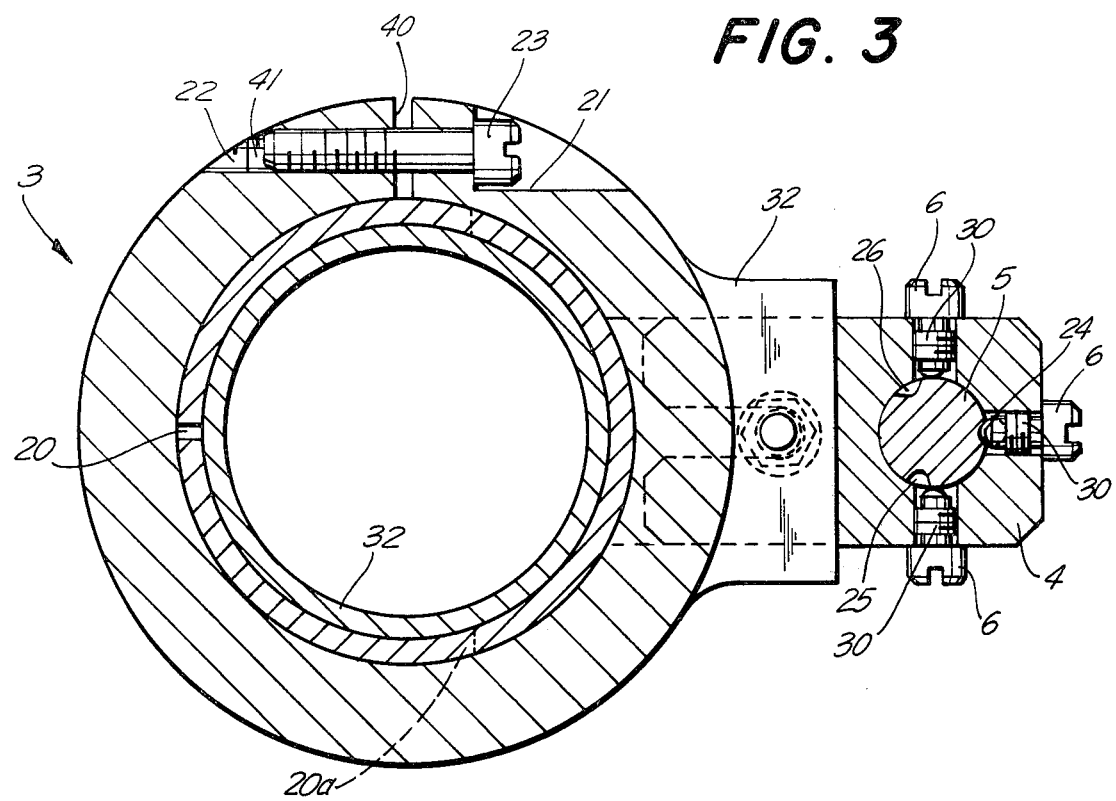
FIG. 3 is a sectional view taken on line 3—3 in FIG. 2.
Figure 4:
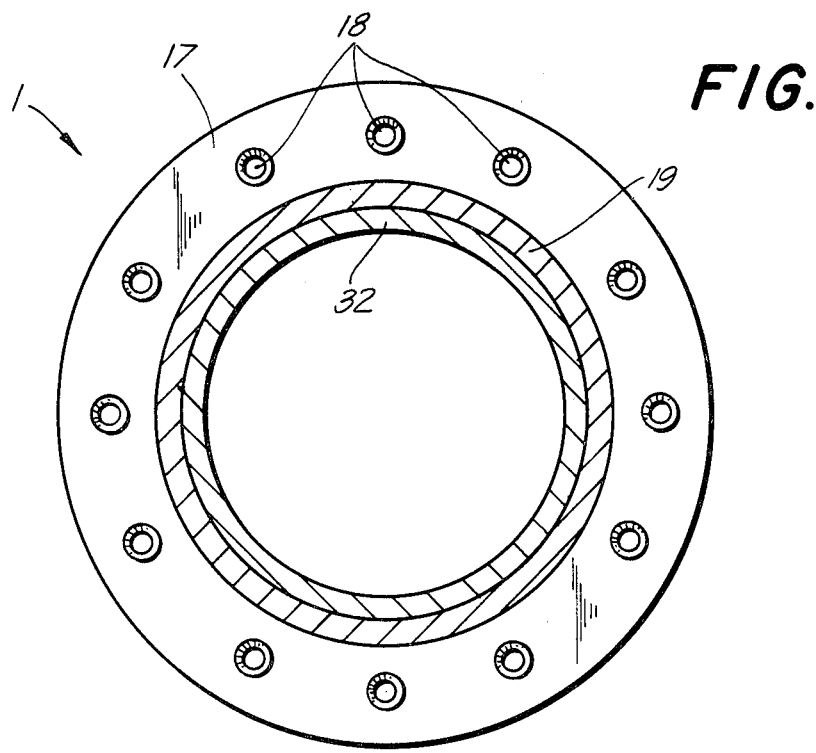
FIG. 4 is a sectional view taken on line 4—4 in FIG. 2.

The ring 1 of the holding device 35 has a cylindrical part 19 with a horizontal slit 20 and a vertical slit 20a. In this way, the cylindrical part 19 has two tongues. These tongues can be pressed inwards, and thus the diameter of the upper part of the cylindrical part can be reduced in certain directions. The ring 1 has a horizontal peripheral flange 17 provided with holes 18 or depressions which are situated substantially 28° from each other. If the ring 1 is to be placed on a long cone of rectangular cross section, a filling element can be placed in the inner wall of the cylindrical part so that the cylindrical part has a rectangular hole for the long cone of utmost rectangular cross section. The utmost outer surface of part 19 of ring 1 extending beyond the slit 20 serves as a slide face for the ring 2 as seen in FIG. 2. The ring 2 has a flange 13 and a groove 14, which are intended to co-operate with a fastening unit 4, which is shown in FIGS. 3 and 5. The fastening unit 4 can be fixed firmly in the groove 14 by means of the screw 50. It should be obvious that the fastening unit can also be made integral with the ring 2. The ring 2 has a hole 12, into which hole a screw 9 has been screwed.

The screw can be of the type shown in FIG. 5 and thus have a hole provided with a bottom where a spring 11 has been arranged, which elastically acts to displace a ball 10 which has been inserted into the hole. When the screw 9 has been screwed in with the spring 11 and the ball 10, the ball will extend slightly from the bottom of the hole 12, but it cannot leave the hole. Due to the elasticity of the spring 11, the ball can be pressed inwards. The ball co-operates with one of the holes 18 in the ring 1. This allows the ring 2 to be brought into several fixed positions, and these are the positions where the ball 10 is in a respective hole 18. The ring 3 is placed on the cylindrical part 19 to act as a locking ring. At its end the locking ring has an inwardly directed, which periphereal flange 39 is intended to rest against the edge of the cylindrical part 19. The locking ring 3 has a slit 40 which makes it possible for the inside periphery of the locking ring to be increased or decreased. The locking ring has a through hole which passes through the slit, and the two hole parts are designated by 21 and 22 in FIG. 3. The hole 22 has a threaded surface 41 for a screw 23. By screwing in the screw 23 the inside periphery of the locking ring 3 can be varied. When the three rings 1, 2, and 3 have been assembled together, the formed holding device 35 is placed upon the long cone 32 in the manner shown in FIG. 1. In this position the screw 23 is screwed in, which has the result that the inside periphery of the locking ring 3 is reduced, and this in turn has the result that the formed tongues on the cylindrical part 19 are pressed against the long cone 32 so that the assembly of the holding device 35 is locked firmly on the long cone. The two rings 2 and 3 together form a peripheral groove with a bottom and two side walls for the ring 2.

The ring 2 can be brought into several fixed positions thanks to the ball 10 and the hole 18. One could even imagine that the friction between the ring 2 and the groove formed is such that the setting can be performed without the presence of the ball and the hole. Instead of the mentioned balls and hole, one could even imagine that either the ring 2 or the groove in which the ring can move is provided with a toothed rim which co-operates with a pin. The teeth can then have a suitable profile so that rotation in a certain direction in steps is allowed, but not in the opposite direction. The teeth can also be of such a type that rotation is allowed in both directions. Another possibility of rotation in steps is to use a toothed rim and a toothed wheel, where the toothed wheel is turned by means of a wheel and is in mesh with the toothed rim.

A groove which facilitates rotation round the axis of the ring 2 and round the axis of the long cone will not necessarily have to be formed by an independent unit, and the outer surface of the long cone 32 can be of such a nature that it can form a guide for the ring 2, in the same way as the two rings 1 and 3.

The fastening unit 4 orientates the bar 5 so that this is always parallel with the axis of the long cone, irrespective of the position of the bar round the long cone. The fastening unit 4 contains a hole 16 for the bar 5, and the fastening unit 4 has three holes 15 placed at 90° from each other, and into these holes a screw 6 is screwed, which has a hole 27 provided with a bottom and which contains a spring 28 and a ball 29. The screw 6 is provided with an outside thread 30. Three such screws 6 are screwed into the fastening unit 4, as appears in FIG. 5. The holes into which the screws have been screwed make it possible for the balls 29 to project into the hole 16. However, it is not possible for the balls to leave the hole 15. But the balls can be pressed back by the springs. The bar 5 has axial grooves 24, 25, and 26, which are placed at 120° from each other. When the bar 5 is turned a ball can snap into the grooves 24, 25, 26 whereas the other balls lie true against the part of the bar 5 which is not provided with a groove. By means of the grooves 24, 25, and 26 and the balls 29, the bar 5 can be turned into several fixed positions, which are kept firm by the engagement between the ball and the groove. Through the existence of the grooves, the bar 5 can be shifted axially at fixed angular positions.

It should be obvious that instead of ball and groove, the fixed positions for the bar 5 in connection with axial shifting and twisting can be obtained through friction between the bar and the fastening unit 4, or by means of racks and pawls. Thus, racks and pawls can be used both in connection with rotation and with axial shifting.

In the end of the bar 5 which is situated in front of the opening of the long cone, there is a hole 31 for co-operation with a pin for the X-ray plate holder 36, as shown in FIGS. 2 and 5. The X-ray plate holder 36 is of such a construction that when an X-ray plate 37 is fastened into a slit in the left-hand end of the X-ray plate holder 36, the X-ray plate 37 is always going to form a right angle with respect to the axis of the long cone.

The present invention is thus drawn to a device which is permanently mounted upon a long cone of an X-ray apparatus, and it is not necessary to dismount the device between various takings of pictures. When the X-ray apparatus is to be used, only an X-ray plate holder 36 is placed in the bar 5, and then the X-ray plate is immediately at a right angle to the axis of the long cone 32, and it is only necessary to turn the ring and the bar so that the plate takes up a suitable position in relation to the patient and so that the plate is situated straight in front of the opening of the long cone. After taking the picture the plate 37 can be developed and the X-ray plate holder 36 can be thrown away. The handling of the device according to the invention is simple and stable, and no sterilization of any parts will be necessary, and it has the advantage that due to the fact that the plate is always at a right angle to the axis of the long cone, an analyst of an exposed film will not have to wonder how the plate was placed during the taking.

A further advantage of the device according to the invention is that it will hardly be necessary to have any re-takings, and therefore the X-ray dose to which the patient is exposed is reduced to a minimum. A further contribution to the reduction of the X-ray dose is the use of a long cone with rectangular cross section, which means that the cross section by and large corresponds to the dimension of the X-ray plate.

What is claimed is:

1. A holding device for an X-ray plate adapted for mounting on an X-ray tube, said holding device comprising ring means mountable on the X-ray tube for turning movement thereon, means for yieldably locking said ring means in a fixed angular position in said tube, a bar, fastening means for attaching said bar to said ring means in a position parallel to the axis of rotation thereof, on said tube, said fastening means including attachment means supporting said bar from said fastening means for longitudinal movement along its axis and for turning movement about said axis, said bar extending forwards from said fastening means and having a front end with means for the detachable support of an X-ray plate holder at right angles to said bar whereby an X-ray plate mounted on said holder assumes a position at right angles to the axis of the tube, said ring means comprising a ring, and first and second ring elements defining a groove in which said ring is rotatably mounted, said first ring element including a flange and a cylindrical part extending from said flange and encircling said X-ray tube, said second ring element being constituted as a slit clamping ring mounted on said cylindrical part, said ring being rotatably mounted on said cylindrical part between said flange of the first ring element and said clamping ring, said means for yieldably locking the ring means comprising resilient engagement means between said ring and said flange for resiliently retaining the ring angularly with respect to said first ring element.

2. A holding device as claimed in claim 1 wherein said cylindrical part of said first ring element has an axial slot and a circumferential slot.

3. A holding device as claimed in claim 1 wherein said resilient engagement means comprises a spring-loaded fastener engaged by said ring, said flange of said first ring element being provided with a plurality of holes arranged in circumferential array, said spring-loaded fastener resiliently engaging said holes in different respective angular positions.

4. A holding device as claimed in claim 1 wherein said fastening means is detachably connected to said ring.

5. A holding device as claimed in claim 1 wherein said bar is frictionally engaged with said fastening means for movement longitudinally and turnably relative thereto and for retention in given position.

6. A holding device as claimed in claim 1 wherein said attachment means for said bar from said fastening means comprises a yieldable element engaging said bar with said fastening means.

7. A holding device as claimed in claim 1 wherein said attachment means comprises a plurality of yieldable elements disposed in angular spacing around said bar and engaged therewith, said bar having a plurality of longitudinal grooves therein disposed at an angular spacing different from that between said yieldable elements, one of said yieldable elements being engageable in one of said grooves.

8. A holding device as claimed in claim 1 wherein the means for the detachable support of said X-ray plate holder to said bar includes male and female engaging elements.

9. A holding device as claimed in claim 8 wherein the X-ray plate holder has a slit for an X-ray plate.

10. A holding device as claimed in claim 9 wherein the X-ray plate holder is made of plastic material.

* * * * *